US009534196B2

(12) United States Patent
Galliher et al.

(10) Patent No.: US 9,534,196 B2
(45) Date of Patent: *Jan. 3, 2017

(54) TEMPERATURE CONTROLLED SUPPORT SURFACES FOR SINGLE USE FLEXIBLE WALL SYSTEMS

(71) Applicant: GE HEALTHCARE BIO-SCIENCES CORP., Piscataway, NJ (US)

(72) Inventors: Parrish M. Galliher, Littleton, MA (US); Thomas Erdenberger, Arlington, MA (US); Colin R. Tuohey, Medway, MA (US); Joseph D. Crowell, South Hamilton, MA (US); Richard L. Damren, Marborough, MA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/367,318

(22) PCT Filed: Jan. 14, 2013

(86) PCT No.: PCT/US2013/021385
§ 371 (c)(1),
(2) Date: Jun. 20, 2014

(87) PCT Pub. No.: WO2013/106809
PCT Pub. Date: Jul. 18, 2013

(65) Prior Publication Data
US 2015/0299641 A1    Oct. 22, 2015

Related U.S. Application Data

(63) Continuation of application No. 13/691,998, filed on Dec. 3, 2012, now Pat. No. 9,340,763, which is a
(Continued)

(51) Int. Cl.
*C12M 3/00* (2006.01)
*C12M 1/00* (2006.01)
(Continued)

(52) U.S. Cl.
CPC .......... *C12M 23/26* (2013.01); *B01F 15/0085* (2013.01); *B01J 19/006* (2013.01);
(Continued)

(58) Field of Classification Search
CPC ........ C12M 23/14; C12M 23/28; C12M 27/20
See application file for complete search history.

(56) References Cited

U.S. PATENT DOCUMENTS 2,915,292 A   12/1959   Gross
3,184,395 A   5/1965    Brewer
(Continued)

FOREIGN PATENT DOCUMENTS

JP    2008501347 A    1/2008
JP    2009539408 A    11/2009
(Continued)

OTHER PUBLICATIONS

First Search Report and First Office Action received for Chinese Patent Application No. CN2013800138161, dated Jul. 21, 2015, 6 pages.
(Continued)

*Primary Examiner* — Nathan Bowers
(74) *Attorney, Agent, or Firm* — Grogan, Tuccillo & Vanderleeden, LLP

(57) ABSTRACT

Disclosed is a heat exchange module for use in a chemical, pharmaceutical or biological reactor system, the module configured to be disposed in the reactor system having a flexible single use container, and including at least one thermally conductive surface adapted to contact the flexible single use container to facilitate heat transfer, and a fluid
(Continued)

circulation path through which a heat exchange fluid can be circulated.

8 Claims, 5 Drawing Sheets

Related U.S. Application Data continuation-in-part of application No. 12/410,724, filed on Mar. 25, 2009, now abandoned.

(60) Provisional application No. 61/586,398, filed on Jan. 13, 2012, provisional application No. 61/566,187, filed on Dec. 2, 2011.

(51) Int. Cl.

| | | |
|---|---|---|
| *C12M 1/02* | (2006.01) | |
| *B01F 15/00* | (2006.01) | |
| *B01J 19/00* | (2006.01) | |
| *B01J 19/18* | (2006.01) | |
| *F28F 3/12* | (2006.01) | |
| *F28F 13/06* | (2006.01) | |
| *F28D 1/06* | (2006.01) | |
| *F28D 1/02* | (2006.01) | |
| *B01J 19/24* | (2006.01) | |
| *B65D 30/08* | (2006.01) | |
| *F16L 11/04* | (2006.01) | |
| *F28D 1/047* | (2006.01) | |
| *F28F 9/013* | (2006.01) | |
| *F28D 7/02* | (2006.01) | |
| *F28D 21/00* | (2006.01) | |
| *F28F 13/00* | (2006.01) | |

(52) U.S. Cl.
CPC ............ *B01J 19/18* (2013.01); *B01J 19/24* (2013.01); *B65D 31/02* (2013.01); *C12M 23/14* (2013.01); *C12M 23/28* (2013.01); *C12M 27/20* (2013.01); *C12M 41/18* (2013.01); *C12M 41/24* (2013.01); *F16L 11/04* (2013.01); *F28D 1/0213* (2013.01); *F28D 1/047* (2013.01); *F28D 1/06* (2013.01); *F28D 7/024* (2013.01); *F28D 7/026* (2013.01); *F28F 3/12* (2013.01); *F28F 9/0131* (2013.01); *F28F 13/06* (2013.01); *B01J 2219/0002* (2013.01); *B01J 2219/0009* (2013.01); *B01J 2219/00081* (2013.01); *B01J 2219/00085* (2013.01); *B01J 2219/00094* (2013.01); *B01J 2219/00765* (2013.01); *B01J 2219/00768* (2013.01); *B01J 2219/24* (2013.01); *F28D 2021/0077* (2013.01); *F28D 2021/0078* (2013.01); *F28F 2013/006* (2013.01); *F28F 2255/02* (2013.01)

(56) References Cited

U.S. PATENT DOCUMENTS

| | | |
|---|---|---|
| 3,963,690 A | 6/1976 | Pruitt et al. |
| 4,282,861 A | 8/1981 | Roark |
| 5,525,311 A | 6/1996 | Girod et al. |
| 6,709,862 B2 | 3/2004 | Curtis |
| 7,077,858 B2 | 7/2006 | Fletcher et al. |
| 2004/0062140 A1* | 4/2004 | Cadogan ............... B01F 7/18 366/144 |
| 2004/0190885 A1 | 9/2004 | Entenman et al. |
| 2005/0272146 A1 | 12/2005 | Hodge et al. |
| 2005/0274499 A1* | 12/2005 | Rule .................. F24H 1/18 165/129 |
| 2006/0165910 A1 | 7/2006 | Kodas et al. |
| 2008/0068920 A1 | 3/2008 | Galliher et al. |
| 2009/0134173 A1* | 5/2009 | Liang ............. B01F 7/00633 220/563 |
| 2009/0242173 A1 | 10/2009 | Mitchell et al. |
| 2010/0015696 A1* | 1/2010 | Claes .............. B01F 3/04269 435/303.3 |
| 2010/0075405 A1 | 3/2010 | Broadley et al. |

FOREIGN PATENT DOCUMENTS

| | | |
|---|---|---|
| JP | 2011509684 A | 3/2011 |
| WO | 2001/78890 A2 | 10/2001 |
| WO | 2008/088371 A2 | 7/2008 |

OTHER PUBLICATIONS

European Search Report for Application No./U.S. Pat. No. 13736189.5-1602/2802645 PCT/US2013/021385, mailed Nov. 24, 2015, 6 pages.
EP Office Action Dated Aug. 2, 2016.

\* cited by examiner

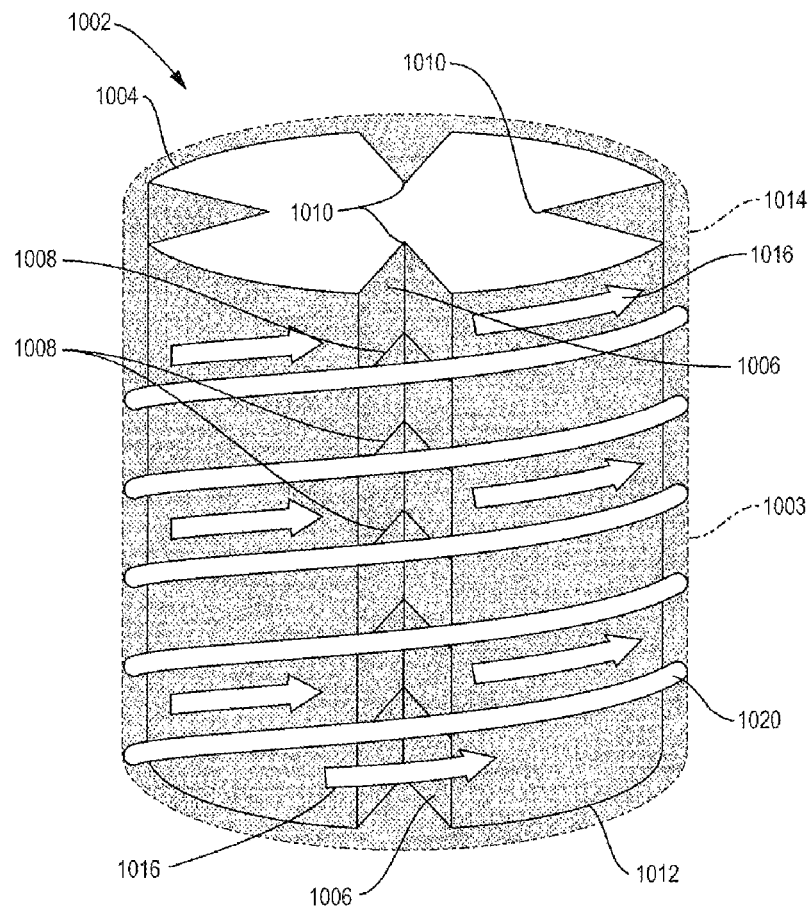
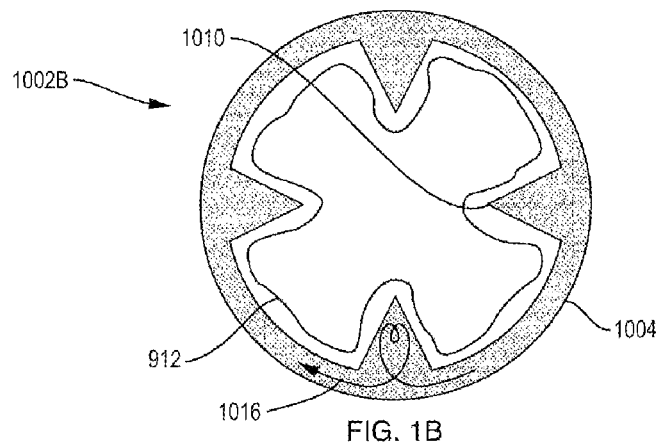

TEMPERATURE CONTROLLED SUPPORT SURFACES FOR SINGLE USE FLEXIBLE WALL SYSTEMS

RELATED APPLICATIONS

This application claims the priority benefit of U.S. Provisional Application No. 61/586,398 filed on 13 Jan. 2012 and U.S. Ser. No. 13/691,998 filed on 3 Dec. 2012. U.S. Ser. No. 13/691,998 also claims the benefit of U.S. Provisional Application No. 61/586,398.

FIELD OF INVENTION

This disclosure relates generally to biochemical processing systems and methods and, in particular, to systems for controlling temperature of a reactor vessel.

BACKGROUND OF THE INVENTION

A variety of vessels for manipulating fluids and/or for carrying out chemical or biological reactions are available. For example, biological materials such as mammalian, plant or insect cells and microbial cultures can be processed using traditional or disposable bioreactors. Although such bioreactors and other fluid manipulating systems incorporating temperature control systems are known, there is a need for improvements to such systems, especially for microbial bioreactors.

Because microbial cultures grow and multiply twenty to forty (20 to 40) times faster than mammalian cells, both the oxygen consumption and the heat evolution rates of a microbial cultures are about 20 to 40 times greater than that of mammalian fermentation processes. In order to sustain growth in microbial cultures, the bioreactor for microbial systems must therefore be able to supply oxygen to the culture fluid and remove heat from the culture fluid 20 to 40 times faster than the oxygen supply and heat removal rates for mammalian cell cultures. This is accomplished in stainless steel microbial fermentors through a number of means, including, e.g., very vigorous agitation by multiple impellers to disperse air bubbles and increase absorption of oxygen by the cells; very high flow rates of air to supply more oxygen; extra cooling surfaces such as cooling coils to remove from the culture fluid the large amount of heat that is generated by the metabolism of the microbial cells and by the frictional heat generated by the vigorous agitation. However, in single-use bioprocessing bags, heat removal is an ongoing problem, especially for microbial bioreactors.

As is well known by those of skill in the field of polymeric or plastic materials such as films and flexible bags, polymeric or plastic films are relatively very poor conductors of heat. Therefore, cooling a fluid inside a vessel containing a replaceable container, e.g., a flexible plastic bag, may require specific modification of the cooling surfaces of the flexible bag and/or the vessel. There is an ongoing need for systems and methods to improve the removal of the large amount of heat generated by microbial cell cultures.

SUMMARY OF THE INVENTION

Methods and apparatus are disclosed for use in a chemical, pharmaceutical or biological reactor system for temperature control. In one aspect, the invention includes a heat exchange module that can be disposed in a reactor system having an inner replaceable reactant container such as, for example, a flexible bag or a semi-rigid container.

One embodiment of the invention is a heat exchange module for use in a chemical, pharmaceutical or biological reactor system having a single use flexible container, the module comprising: a body having a central chamber configured for receiving the single use flexible container and configured to be disposed in a reactor vessel, the body comprising: an outer surface configured to conform to a shape of the reactor vessel; at least one thermally conductive surface adapted to contact the single use reactant container to facilitate heat transfer; and at least one integral strong baffle forming a protrusion into the central chamber; wherein the body is an elongate body having a top end and a bottom end and is adapted to be inserted into the reactor vessel such that the body extends at least a substantial portion of the distance between a top and a bottom of the reactor vessel, and a heat exchanger disposed at the outer surface of the body, the heat exchanger comprising a fluid circulation path through which a heat exchange fluid can be circulated around the circumference of the body and into and out of a channel in the at least one strong baffle, such that when the flexible container is inserted into the chamber, a fluid within the flexible container is heated or cooled by the heat exchange fluid and baffled by the at least one strong baffle.

In one embodiment of the invention, the heat exchange module body is configured to extend to a position opposite an impeller positioned at or near the bottom of the single use flexible container, and the at least one integral strong baffle is configured to baffle a shear field produced by the impeller.

Another aspect of the invention is a container chosen from a flexible bioreactor bag, a flexible mixer bag, and a flexible tubing, the container comprising at least one double wall portion comprising an inner and an outer wall and a heat conductive material attached to or embedded in a portion of at least one of the inner wall and the outer wall.

Yet another aspect of the invention is a flexible polymeric wall chosen from a bioreactor wall, a mixer wall, and a tubing wall, the flexible wall comprising a heat conductive material attached to or embedded in a portion of the flexible wall.

Yet another embodiment the invention is a jacketed, tiered baffle, bioreactor tank comprising: an outer cylindrical-shaped jacket; and a cylindrical tank having an inner tank surface defining a chamber configured for supporting a flexible bag disposed within the chamber, and an outer tank surface having tiered baffles configured for routing a heat exchange fluid around the entirety of the outer tank surface, the cylindrical tank disposed axially within the outer cylindrical-shaped jacket, wherein the outer cylindrical-shaped jacket is sealed to the cylindrical tank in a manner sufficient to prevent or minimize loss of the heat exchange fluid.

BRIEF DESCRIPTION OF THE DRAWINGS

The foregoing and other non-limiting objects, features and advantages of the invention will be apparent from the following more particular description of illustrative embodiments of the invention, as illustrated in the accompanying drawings in which like reference characters refer to the same parts throughout the different views. The drawings are schematic and not intended to be drawn to scale, emphasis instead being placed upon illustrating the principles of the invention. The drawings are schematic and not intended to be drawn to scale, emphasis instead being placed upon illustrating the principles of the invention. The features illustrated or described in connection with one exemplary embodiment can be combined with the features of other embodiments. Such modifications and variations are intended to be included within the scope of the present invention.

FIG. 1A is a perspective view of a schematic representation of an exemplary heat exchange module having a serpentine flow path for a heat exchange liquid, and a partial cut-away view of an outer support structure or outer vessel wall.

FIG. 1B is a top plan view of the heat exchange module shown in FIG. 1A, and depicting the heat exchange fluid flow path into and out of the interior of a strong baffle integrated with the inner support wall.

DETAILED DESCRIPTION

Figure 2:
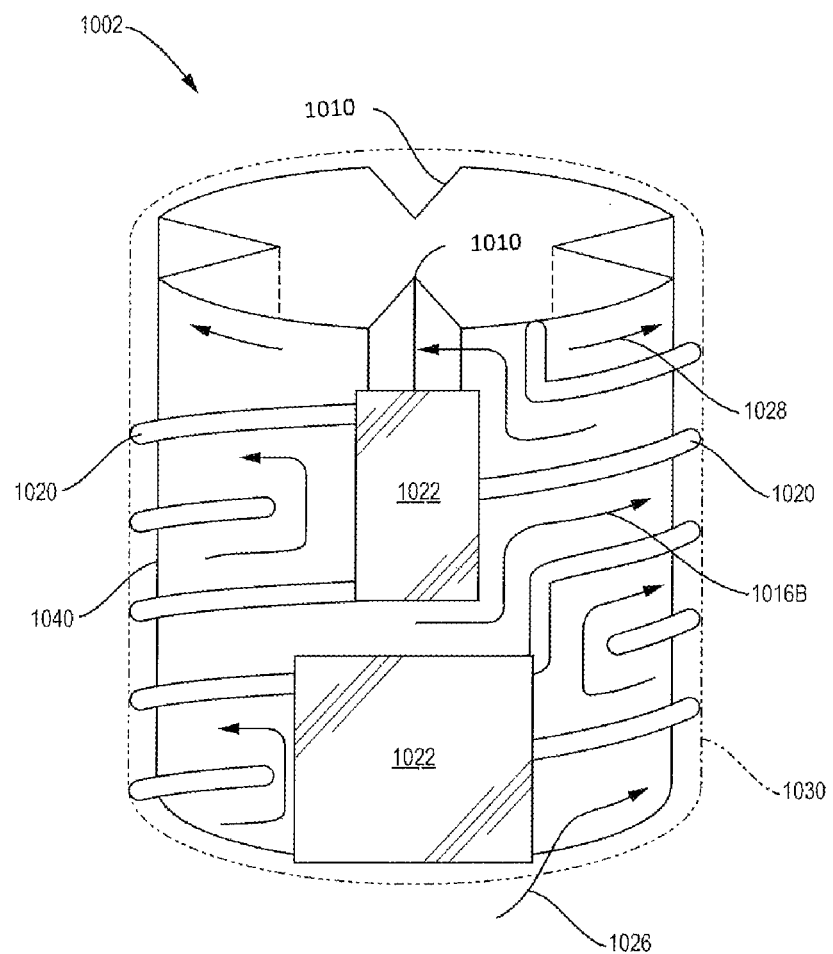
FIG. 2 is a perspective view of an exemplary heat exchange module having a non-linear flow path within a tiered baffle structure; an opening configured for alignment with a window; and a partial cut-away view of an outer support structure or outer vessel wall.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "e.g.," and "in one embodiment."

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but can include other elements not expressly listed or inherent to such process, article, or apparatus. Further, unless expressly stated to the contrary, "or" refers to an inclusive or and not to an exclusive "or."

Disclosed herein are systems and methods for containing and manipulating fluids, and for regulating the temperature of fluids associated with a chemical, biological, or pharmaceutical reaction or process. Certain embodiments of the invention involve a series of improvements and features for fluid containment systems, for example, by providing a support structure or rigid vessel including a heat exchanger, the rigid vessel surrounding and supporting a container or liner that can be in the form of a flexible, collapsible bag or a rigid, or semi-rigid container. Some embodiments of the invention include hollow baffles (interior or exterior to the liner, or both) through which a temperature control fluid such as a coolant is circulated.

The Vessel or Support Structure

The terms "supporting structure," "support structure," "vessel," and "tank" are used herein interchangeably. A support structure that can be used to support a collapsible bag can have any suitable shape able to surround and/or contain the bag. In some cases, the support structure is reusable. The support structure can be formed of a substantially rigid material. Non-limiting examples of materials that can be used to form the support structure include stainless steel, aluminum, glass, resin-impregnated fiberglass or carbon fiber, polymers such as high-density polyethylene, polyacrylate, polycarbonate, polystyrene, nylon or other polyamides, polyesters, phenolic polymers, and combinations thereof. The materials can be certified for use in the environment in which it is used. For example, non-shedding materials can be used in environments where minimal particulate generation is required. In addition, the support structure can include other components, such as channels, for flowing a fluid and/or containing a material to modify the properties of the support structure.

A reusable support structure or vessel can have any suitable volume and, in some instances, has a volume substantially similar to that of the container contained in the support structure. The reusable support structure can have a volume between, for example, of from about 5 liters to about 5,000 liters. Volumes greater than 10,000 liters are also possible.

The term "vessel" as used herein generally refers to a support structure or tank surrounding and supporting a flexible bag. The term vessel is intended to encompass bioreactor vessels as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. In the bioprocessing industry, the term "vessel" is often used to define any enclosed bioprocessing volume in which the regulation of temperature is desirable.

The Flexible Bag or Container

The terms "rigid" and "semi-rigid" are used herein interchangeably to describe structures that are "non-collapsible," that is to say structures that do not fold, collapse, or otherwise deform under normal forces to substantially reduce their elongate dimension. Depending on the content "semi-rigid" can also denote a structure that is more flexible than a 'rigid' element, e.g., a bendable tube or conduit, but still one that does not collapse longitudinally under normal conditions and forces. The terms "flexible container," "flexible bag," "collapsible bag," "bag," and "container," as used herein, are used synonymously. A bag or flexible container or flexible bag is a container that is unable to maintain its shape and/or structural integrity when subjected to the internal pressures, for example, pressures resulting from the weight or hydrostatic pressure of liquids or gases contained therein without the benefit of a separate support structure. A reusable support structure such as a rigid vessel or tank can be utilized to surround and support a collapsible bag.

As described herein a container such as a collapsible bag can include a mixing system for mixing contents of the bag. In some cases, more than one agitator or impeller can be used to increase mixing power, and the impellers can be the same or different. In some cases, the agitator can be one in which the height can be adjusted, for example, such that the drive shaft allows raising of an impeller above the bottom of the container and/or allows for multiple impellers to be used. A mixing system of a container can be disposable or intended for a single use, along with the container in some cases. Various methods for mixing fluids can be implemented in the container. For instance, impellers based on magnetic actuation, sparging, and/or air-lift can be used. Direct shaft-drive mixers that are sealed and not magnetically coupled can also be used. Additionally or alternatively, a mixing system can include an impeller with varying impeller blade configurations.

Many disclosed examples include the use of collapsible bags, liners, or flexible containers. In addition, an embodiment of the invention can include systems utilizing non-collapsible bags, rigid containers, semi-flexible containers and other configurations involving liquid containment.

The collapsible bag can be made out of inherently flexible materials, such as many plastics, or can be made out of what are normally considered rigid materials such as glass or certain metals, but having a thickness or other physical properties rendering the container as a whole unable to maintain its shape or structural integrity when subjected to the internal pressures expected during operation without the benefit of a separate support structure. In some embodiments, collapsible bags include a combination of flexible materials and substantially rigid materials such as a rigid polymer, metal, or glass. For example, the collapsible bag, liner or other container can include rigid components such as connections, ports, supports for a mixing and/or antifoaming system.

In some embodiments, a rigid or semi-rigid container or a collapsible bag comprises a polymeric material, for example, as a bulk material. Polymeric materials, such as the ones described herein, can be selected or formulated to have suitable physical and mechanical characteristics, for example, by tailoring the amounts of components of polymer blends to adjust the degree of any expected cross-linking. For instance, those of ordinary skill in the art can choose suitable polymers for use in containers based on factors such as the polymer's thermal conductivity, compatibility with certain processing techniques, compatibility with thermally-conductive materials, compatibility with any materials, such as cells, nutrients, solvents, contained in the container, and compatibility with sterilizations or other treatments or pre-treatments associated with performing a reaction inside the container.

In some embodiments, a collapsible bag is formed of a suitable flexible material, such as a homopolymer or a copolymer. The flexible material can be one that is USP Class VI certified, for example, silicone, polycarbonate, polyethylene, and polypropylene. Non-limiting examples of flexible materials include polymers such as polyethylene (for example, linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. Portions of the flexible container can comprise a substantially rigid material such as a rigid polymer, for example, high density polyethylene, metal, or glass. Substantially rigid materials can be utilized in areas for supporting fittings, for example.

In other embodiments, the container is a substantially rigid material. Optionally, all or portions of the container can be optically transparent to allow viewing of contents inside the container. The materials or combination of materials used to form the container can be chosen based on one or more properties such as flexibility, puncture strength, tensile strength, liquid and gas permeability, opacity, and adaptability to certain processes such as blow molding for forming seamless collapsible bags. The container can be single use or disposable in some cases.

The container can have any suitable thickness for holding a liquid and can be designed to have a certain resistance to puncturing during operation or while being handled. The thickness of a material such as a container wall is often specified in "mils" A mil is a unit of length equal to one thousandth ($10^{-3}$) of an inch, which is equivalent to 0.0254 millimeter. The unit "millimeter" is abbreviated herein as "mm." For example, a thickness of the flexible wall portions of a collapsible bag suitable for use in an embodiment of the invention can be less than 10 mils (less than 0.254 mm), or from about 10 mils to about 100 mils (from about 0.254 mm to about 2.54 mm) or from about 15 mils to about 70 mils (from about 0.38 mm to about 1.78 mm), or from about 25 mils to about 50 mils (from about 0.64 mm to about 1.27 mm). In yet another example, the walls of a container can have a total thickness of about 250 mils.

In some embodiments, the container includes more than one layer of material that can be laminated together or otherwise attached to one another in order to impart certain properties to the container. For instance, one layer can be formed of a material that is substantially oxygen impermeable. Another layer can be formed of a material to impart strength to the container. Yet another layer can be included to impart chemical resistance to a fluid that may be contained in the container. One or more layers of the container can include a thermally-conductive material to facilitate heat transfer to and from the interior of the container to an environment outside of the container, as described in more detail below.

A container, liner, or other article disclosed herein can be formed of any suitable combinations of layers. Non-limiting examples include an article comprising from 1 layer to about 5 layers of the same or different materials. Each layer can have a thickness of, for example, from about 3 mils to about 200 mils (from about 0.076 mm to about 5.08 mm), or combinations thereof.

Components that are integrated with collapsible bags or other containers can be formed in any suitable material, that may be the same or different from the material of the bag or container. In one embodiment, a container is formed in a first polymer and a component is formed in a second polymer that is different, for example, in composition, molecular weight, or chemical structure, from the first polymer. Those of ordinary skill in the art will be familiar with material processing techniques and will be able to use such techniques in the methods described herein to choose suitable materials and combinations of materials.

A rigid container or a collapsible bag suitable for use in an embodiment of the invention can have any size for containing a liquid. For example, the container can have a volume from about 0.1 liter to about 10,000 liters (from about 100 cubic centimeters to about $1\times10^7$ cubic centimeters.) The term "cubic centimeter" will be abbreviated herein as "$cm^3$." In other non-limiting examples, the container can have a volume from about 5 liters to about 5,000 liters (from about 5,000 $cm^3$ to about $5\times10^6$ $cm^3$), or from about 40 liters to about 1,000 liters (from about $4\times10^4$ $cm^3$ to about $1\times10^6$ $cm^3$). Volumes greater than 10,000 liters ($1\times10^7$ $cm^3$) are also possible. The suitable volumes can depend on the particular use of the container. For example, a collapsible bag used as a heat exchanger can have a smaller volume than a collapsible bag used to hold and store a large amount of fluid.

If a collapsible bag is used, it can be substantially deflated prior to being filled with a liquid, and can begin to inflate as it is filled with liquid. In other embodiments, the invention can include open container systems.

In some embodiments, seamless collapsible bags can be made specifically to fit a particular reusable support structure having a unique shape and configuration. Substantially perfect-fitting collapsible bags can be used, for example, as part of a bioreactor system or a biochemical or chemical reaction system. Seamless rigid or semi-rigid containers can also be beneficial in some instances.

Additional description of seamless containers can be found in U.S. patent application Ser. No. 11/818,901, filed Jun. 15, 2007, entitled, "Gas Delivery Configurations, Foam Control Systems, and Bag Molding Methods and Articles for Collapsible Bag Vessels and Bioreactors," by G. Hodge, et al., published as US2008/0068920 A1 on Mar. 20, 2008, the entire teachings of which are incorporated herein by reference.

The invention is described in more detail in the following examples, which are provided by way of illustration and are not intended to limit the invention in any way.

Disclosed herein is a system for controlling the temperature of the contents of a container such as a collapsible bag while allowing a desired process such as a chemical, biochemical or biological reaction to occur in a liquid phase within the bag. The collapsible bag can also be configured such that a liquid, such as liquid media including suspended cells, remains substantially in contact only with the collapsible bag during use and not in contact with support structure. In such embodiments, the collapsible bag can be disposable and used for a single reaction or a single series of reactions, after which the bag is discarded. Because the liquid in the collapsible bag in such embodiments does not come into contact with the support structure, the support structure can be reused without cleaning. After a reaction takes place in the bag, the bag can be removed from the reusable support structure and replaced by a second single use or disposable container. A second reaction can be carried out in the second container without having to clean either the first container or the reusable support structure.

One or more optional inlet ports and one or more optional outlet ports can be formed in the container and/or the reusable support structure or vessel, and can facilitate more convenient introduction and removal of a liquid or gas from the container. For example, a plurality of inlet ports positioned in any suitable location with respect to the bag can be used to provide different gas compositions via a plurality of spargers. Tubing can be connected to the inlet and outlet ports to form delivery and harvest lines, respectively, for introducing and removing liquid from the container. Ports in the container can also be used for sampling, determining and/or analyzing conditions such as pH or the amount of dissolved gases in the liquid within the container or for other purposes. Optionally, the system can include a utility tower that facilitates interconnection of one or more devices internal to the container or support structure with one or more pumps, controllers, or electronics, such as sensor electronics, electronic interfaces, and pressurized gas controllers or other devices. Such devices can be controlled using a control system.

In general, as used herein, a component of an inventive system that is "operatively associated with" one or more other components indicates that such components are directly connected to each other, in direct physical contact with each other without being connected or attached to each other, or are not directly connected to each other or in contact with each other, but are interconnected mechanically, electrically, fluidically, or remotely via electromagnetic signals, so as to cause or enable the components so associated to perform their intended functionality.

Heat Exchange Modules in Reactor Systems

As will be explained in further detail below, the disclosed reactor systems are equipped with a heat exchange module, which can include a body configured to be disposed in the reactor system having an inner replaceable reactant container, the body further including at least one thermally conductive surface adapted to contact the inner container to facilitate heat transfer, and a heat exchanger disposed at the module body having a fluid circulation path through which a heat exchange fluid can be circulated.

The terms "reactor" and "reactor system" are used interchangeably herein and are intended to encompass chemical, pharmaceutical and biological reactors, including but not limited to cell culturing and vaccine producing reactors, as known in the art. Although much of the description herein involves exemplary applications of the present invention related to bioreactors and chemical, reaction systems, the invention and its uses are not so limited, and it should be understood that aspects of the invention can also be used in other settings, including those involving containment systems in general, as well as systems for containment or for mixing or other processing.

As will be detailed below, a heat exchange module for use in a chemical, pharmaceutical or biological reactor system can include a body configured to be disposed in the reactor system between an outer support structure and an inner replaceable reactant container. In some embodiments the heat exchanger module is integral with the inner wall of a support vessel. The body can further include at least one thermally conductive surface adapted to contact the inner replaceable reactant container to facilitate heat transfer. Furthermore, the heat exchange module can include a heat exchanger disposed within the module body and can include a fluid circulation path through which a heat exchange fluid can be circulated. A heat exchange module can be removable from the reactor system or can be integrally formed with the reactor support structure. A heat exchange module can also be formed so as to provide increased mixing to a fluid in the interior replaceable container or to fluid circulating in the vessel. Increased mixing can increase the efficiency of heat transfer in the reactor system.

In other embodiments, however, a reactor system does not include a separate container, for example, a collapsible bag and support structure, but instead comprises a self-supporting disposable container. For example, a container that can be used to hold and/or store fluids can be in the form of a plastic vessel and can optionally include an agitation system integrally or releasably attached thereto. The agitation system can be disposable along with the container. In one particular embodiment, such a system includes a magnetic impeller positioned in a polymeric container or a flexible bag and held in place by an external magnetic drive system. In another embodiment, a container that is used as a heat exchanger is in the form of a rigid container. It should therefore be understood that many of the aspects and features of the vessels described herein with reference to a container and a support structure are also applicable to a self-supporting disposable container.

A reactor system typically can include a temperature control system (not shown in the drawings) that includes a thermocouple and/or a resistance temperature detector for sensing a temperature of the contents inside a reaction container. The thermocouple can be operatively connected to the temperature controller/heat exchanger to control temperature of the contents in the container. Optionally, as described herein, a thermally-conductive material can be associated with a surface of the container in order to provide a heat transfer surface that tends to overcome the insulating effect of the polymeric material typically used to form portions of the container.

As used herein, the term "temperature-controlling surface" has the same meaning as "heat transfer surface." The temperature of the fluid flowing in a collapsible bag can be changed, in one embodiment, by associating one or more surfaces of the collapsible bag with a heat transfer surface, for the purpose of promoting transfer of heat to and/or from the collapsible bag.

In some cases, the rate of heat exchange is limited below desirable or optimal levels by the material used to form a heat transfer surface or container. For instance, systems involving the use of disposable liners in the form of collapsible bags are generally made of low thermally-conductive materials such as polyethylene, polytetrafluoroethylene (PTFE), or ethylene vinyl acetate. Additionally or alternatively, the thermally-conductive material can line a wall of the container. For instance, the thermally-conductive material and the wall of the container can form a laminate structure.

Figure 4A:
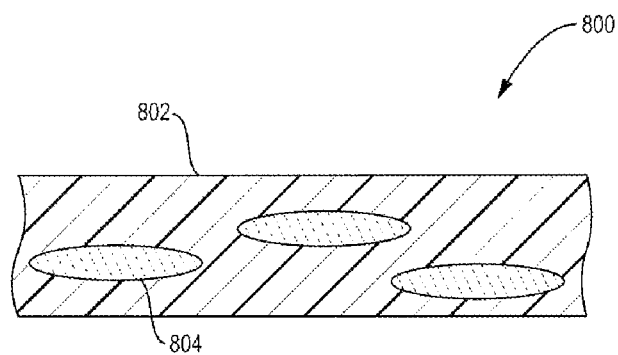
FIG. 4A is a sectional view of an inner or outer tubing surface or an inner or outer bag film surface having sections of heat conductive material attached to or embedded in the film.
Figure 4B:
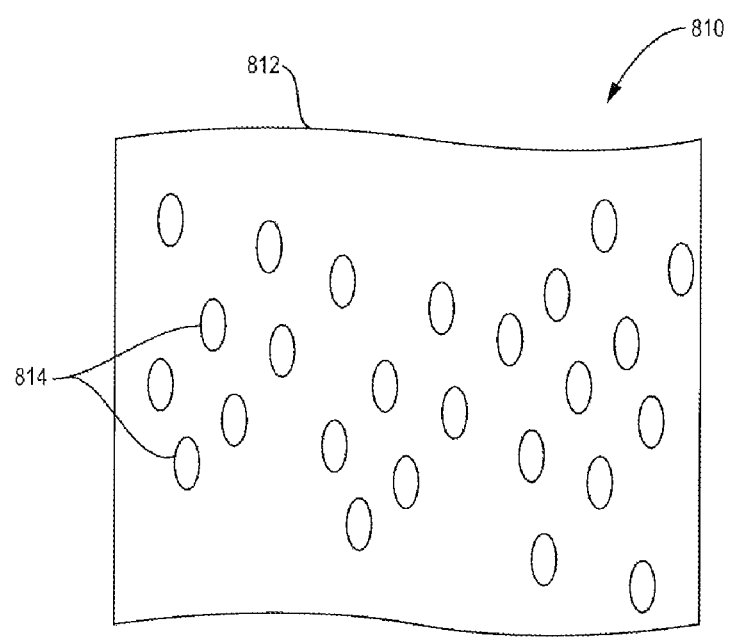
FIG. 4B is sectional view of an inner or outer tubing surface or an inner or outer bag film surface having sections of heat conductive material attached to or embedded in the film.

To enhance heat conduction, a temperature-controlling surface can comprise a thermally conductive surface formed of a thermally conductive material, such as, e.g., a plurality of particles 804, 814, FIGS. 4A and 4B, respectively. The particles 804, 814 are attached to or embedded in a surface of a flexible polymeric tubing 802 in a section of a tubing 800, or a surface of a film 812 in a section of a flexible bag 810, respectively. The tubing 802 and the bag 810 can be single-walled or double-walled, and in the case of a double-wall, the thermally conductive material can be embedded in or attached to at least one of the inner or the outer wall. A temperature-controlling surface can comprise a thermally conductive plate comprising channels for allowing fluid to flow therethrough, channels for allowing fluid to flow therethrough wherein the channels are not associated with a plate, and combinations of the foregoing.

In some embodiments, the thermally-conductive material is in the form of a plurality of particles. The particles can be in the form of nanoparticles, microparticles, powders, and the like. The thermally-conductive material can also be in the form of nanotubes, nanowires, nanorods, fibers, meshes, or other entities. The thermally-conductive material can be embedded in the material used to form the container, for example, such that all or a portion of each entity is enveloped or enclosed by the material used to form the container.

In some embodiments, an embedded thermally-conductive material is substantially uniformly dispersed throughout a bulk portion of a material used to form a container. "Substantially uniformly dispersed," in this context, means that, upon viewing a cross-sectional portion of any such material, where the cross-section comprises the average makeup of a number of random cross-sectional positions of the material, investigation of the material at a size specificity, for example, on the order of grains, or atoms, reveals essentially uniform dispersion of the thermally-conductive material in the bulk material. A photomicrograph, scanning electron micrograph, or other similar microscale or nanoscale investigative process may reveal essentially uniform distribution.

It should be understood that in other embodiments, a thermally-conductive material is not substantially uniformly dispersed throughout a bulk portion of the material used to form a heat transfer surface. For example, a gradient of particles can be formed across a cross-section of the heat transfer surface. For example, the thermally-conductive material can be configured such that one portion of the heat transfer surface includes a thermally-conducive material and another, adjacent portion of the container or heat exchange module also comprises the thermally-conductive material. Alternatively, the thermally-conductive material can be present as strips, wires, or can have other configurations such that one portion of the heat transfer surface includes a thermally-conducive material and another, adjacent portion of the container or heat exchange module does not comprise a thermally-conductive material.

The thermally-conductive material can in certain embodiments be encapsulated between two polymeric sheets. Alternating layers of thermally-conductive material and polymeric layers are also possible. Alternatively, in some embodiments, an outer surface of the container or liner can include a layer of thermally-conductive material, while an inner surface of the container or liner does not include the thermally-conductive material. This configuration can allow heat to be conducted away from (or into) the contents of the container or liner, while avoiding or limiting any reactivity between the contents of the container or liner and the thermally-conductive material. For example, silver has a high thermal conductivity and can be used as a thermally-conductive material, but is known to have antimicrobial effects. By positioning the silver at an outer surface of the container (or embedded between two polymer layers), but not in contact with any contents inside the container, heat conduction of the container can be enhanced without adversely affecting the contents inside the container (for example, cells, proteins, etc.).

The thermally-conductive material may have any suitable size or dimension. The size of the thermally-conductive entities can be chosen, for example, to achieve a certain dispersion, for example, a gradient or a substantially uniformly dispersion, within the bulk material used to form the heat transfer surface, to prevent protrusion of the entity through a portion of the container, or to have a certain surface area or thermally conductive material to volume ratio. For example, the thermally-conductive material may have at least one cross-sectional dimension less than 500 microns, or in another embodiment less than 1 nanometer.

Any suitable thermally conducting material can be used as a thermally-conductive material in an embodiment of the invention. The thermally-conductive material can be chosen based on factors such as its thermal conductivity, particle size, magnetic properties, compatibility with certain processing techniques, for example, ability to be deposited by certain deposition techniques, compatibility with the bulk material used to form the container, compatibility with any materials contained in the container, compatibility with any treatments or pre-treatments associated with performing a reaction inside the container, as well as other factors.

In one set of embodiments, the thermally-conductive material comprises a metal. In other cases, the thermally-conductive material comprises a semiconductor. Materials potentially suitable for use as thermally-conductive materials include, for example, an element in any of Groups 1-17 of the Periodic Table. Typical examples include a Group 2-14 element, or a Group 2, 10, 11, 12, 13, 14, 15 element. Non-limiting examples of potentially suitable elements from Group 2 of the Periodic Table include magnesium and barium; from Group 10 include nickel, palladium, or platinum; from Group 11 include copper, silver, or gold; from Group 12 include zinc; from Group 13 include boron, aluminum, and gallium; from Group 14 include carbon, silicon, germanium, tin, or lead. In some cases, the thermally-conductive material is aluminum, copper, iron, or tin.

The thermally-conductive material can comprise one or more metals. Similarly, where the thermally-conductive material comprises a semiconductor, one or more semiconducting materials can be used. Additionally, alloys can be used, and a mixture of metals and semiconductors can be used. That is, the thermally-conductive material can be a single metal, a single semiconductor, or one or more metals or one or more semiconductors mixed. Non-limiting examples of suitable metals are listed above, and suitable components of semiconductors are listed above. Those of ordinary skill in the art are well aware of semiconductors that can be formed from one or more of the elements listed above, or other elements.

In certain cases, the thermally-conductive material is a nonmetal. For example, the thermally-conductive material can comprise carbon. The thermally-conductive material can be in the form of a conductive polymer, for instance. Non-limiting examples of conductive polymers include polypyrroles, polyanilines, polyphenylenes, polythiophenes, and polyacetylenes.

Those of ordinary skill in the art can easily select, without undue burden or undue experimentation, from materials described above or other materials known in the field, suitable metals, semiconductors, and/or nonmetals. The teachings described herein also enable those of skill in the relevant art to screen materials for suitable use in connection with embodiments described herein. Optionally, thermally-conductive materials can be coated or treated to enhance certain chemical or physical properties of the materials. For example, the surfaces of the thermally-conductive materials can be treated with a surfactant, an oxide or any other suitable material, to make the materials more hydrophilic, more hydrophobic, less reactive, have a certain pH, and so forth. These and other processes can allow the thermally-conductive materials to be more compatible with the material used to form the container and/or with certain processing techniques. For example, treatment of the thermally-conductive material can allow it to adhere to the material used to form the container to a desired degree, be more soluble in a particular solvent, or be more dispersible.

In some embodiments, a system of the invention includes a heat exchange module adapted to contact the bag. Advantageously, a heat exchanger module can be utilized in systems experiencing said undesirable heat transfer characteristics. The heat exchanger module can be formed and configured such that a thermally-conductive material is adapted to conduct heat away from an interior of the container to an environment outside of the container, or to conduct heat into the container from an environment outside of the container. In embodiments in which the container is supported by a reusable support structure, for example, thermally-conductive plates or a stainless steel tank, heat conduction away from or into the container can be facilitated by the heat exchange module coupled to the support structure. For instance, heat from the contents inside the container can be dissipated, via the thermally-conductive material of the container, to the support structure which can also be thermally-conductive.

The heat exchange module can facilitate heat transfer with the inner container and can be used to change the temperature of a fluid to varying degrees. For instance, the temperature of a fluid can be varied by at least 2° C., at least 5° C., at least 10° C., at least 15° C., at least 20° C., or at least 30° C.

In some embodiments, the heat exchange module can be formed in the wall of the vessel or support structure providing a temperature regulating jacket to the inner container. In these embodiments, a protrusion can extend into the interior of the support vessel, such that when the flexible container is inserted into the support structure vessel, the fluid inside the flexible container is both baffled and temperature regulated. By baffling the inner container, mixing within the container can be improved. This integral system provides physical support for the flexible container, temperature regulation of the reactor system, and can provide increased mixing. This integral cooling baffle support structure can be in the form of a vessel, integral liner, a flat plate system, or any other integral configuration.

It should be understood that not all of the features shown in the figures need be present in all embodiments of the invention and that the illustrated elements can be otherwise positioned or configured. Also, additional elements can be present in other embodiments.

FIG. 1A is a perspective view of a schematic representation of an exemplary heat exchange module 1002 having a serpentine fluid flow path 1016, and a partial cut-away view of an outer support structure or outer vessel wall 1003. FIG. 1B is a top plan view 1002B of the heat exchange module 1002 shown in FIG. 1A, and depicting the heat exchange fluid flow path 1016 into and out of the interior of a strong baffle 1010 integral with the inner wall 1004 of the vessel.

FIGS. 1A and 2 depict embodiments wherein the heat exchanger module 1002 is integrally formed with the outer support structure or outer vessel wall 1003 (shown in phantom), and a temperature control fluid flow path 1016, 1016B, respectively, is formed between the outer vessel wall 1003 and the surface of the inner wall 1004, 1040, respectively, of the vessel. In FIGS. 1A and 1B, the direction of the temperature control fluid is shown by arrows 1016; and the spaces filled with the temperature control fluid are shown by speckling or shading between the inner vessel wall 1004 and the outer vessel wall 1003. Protrusions or integral strong baffles 1010 are shown projecting into the central chamber defined by the inner vessel wall 1004. FIG. 1B shows that the fluid flows 1016 into the baffle channels 1006 and out again. FIG. 1B also shows that the flexible bag 912 positioned within the central chamber of the heat exchanger module body 1004 conforms to the shape of the strong baffles 1010, such that the strong baffles 1010 provide baffling within the flexible bag 912. Such baffling is known to greatly improve mixing within the bag 912.

FIG. 1A shows that the heat exchange module 1002 having an integral strong baffle 1010 provides a non-linear fluid flow path 1016 that is formed by various separator plates 1008 disposed vertically along the baffle channels 1006. In this embodiment the inner vessel wall 1004 of the heat exchanger module 1002 is again integrally formed on an outer vessel wall 1003. The inner vessel wall 1004 includes integral strong baffles 1010 protruding into the interior of the vessel, the strong baffles 1010 forming baffle channels 1006. Temperature control fluid can circulate along a path between the outer vessel wall 1003 and the inner vessel wall of the body 1004, including through the baffle channels 1006. Separator plates 1008 can be formed along the length of the baffle channel 1006 so as to direct the flow of fluid in a desired path. In the baffle channel 1006, the separator plates 1008 will stop fluid from flowing vertically from the bottom 1012 of the heat exchange module 1002 to the top 1014 of the heat exchange module 1002 or from the top to the bottom. One skilled in the art will recognize the advantages of directing the fluid flow pattern around the heat exchange module 1002 to achieve the desired heat transfer characteristics for the system.

In some embodiments, the fluid flow path 1016 within the heat exchange module 1002 can be directed in a non-linear direction concentrically around the heat exchanger module 1002. FIG. 1A depicts a spiral channel structure formed by protrusions 1020 to direct the temperature control fluid around the heat exchange module 1002. Separator plates 1008 can be used to block vertical fluid flow through the baffle channels 1006 to prevent fluid from flowing vertically through the baffle 1006, which could short cut the remainder of the jacket. The spiral channel can be formed integrally with the inner vessel wall 1004 between protrusions 1020, or can be formed removably and separately from the inner vessel wall 1004. The spiral channel can be formed between a strip, tube, pipe, or other protrusion 1020 formed of metal, plastic, or any other non-porous, non-corrosive material, disposed in a concentric loop through the heat exchange module 1002 to direct fluid along a path 1016. The fluid circulation path 1016 should preferably reach the strong baffle channels 1006 to ensure the desired amount of temperature control therein. In other embodiments a tiered channel structure can be used to create a non-linear fluid circulation path.

FIG. 2 is a perspective view of an exemplary heat exchange module 1002 having at least one strong baffle 1010 and a tiered channel structure formed by protrusions 1020 with a non-linear flow path 1016B and at least one opening 1022 configured for alignment with a window or door in the outer vessel wall 1030 (shown in phantom). A tiered, or terraced, baffled interior channel structure formed between the inner vessel wall 1040 and the outer vessel wall 1030 formed by protrusions 1020 is shown in FIG. 2. The interior channel structure directs temperature control fluid in a non-linear manner around the heat exchanger module 1002 and into the interior of the strong baffles 1010 protruding into the interior chamber formed by the inner vessel wall 1040. In this embodiment the fluid follows the non-linear path 1016B. The channel structure can have a fluid inlet 1026 at the bottom of the heat exchange module 1002 and an outlet 1028 at the top of the heat exchange module 1002, or alternatively, the heat exchange module 1002 can have temperature control inlet 1026 and outlet 1028 ports at any position so as to achieve the desired heat transfer results. As is shown, the heat exchange module 1002 can be formed to accommodate sight windows 1022 into the interior of the reactor system allowing an operator to monitor the reaction. The terraced baffle structure can allow the temperature control fluid circulation path to be directed around said sight windows 1022 to avoid the obstruction of the sight path. This non-linear circulation path 1016B can also allow any access ports or probes to be accessible to the outer vessel wall 1030 as necessary.

Figure 3:
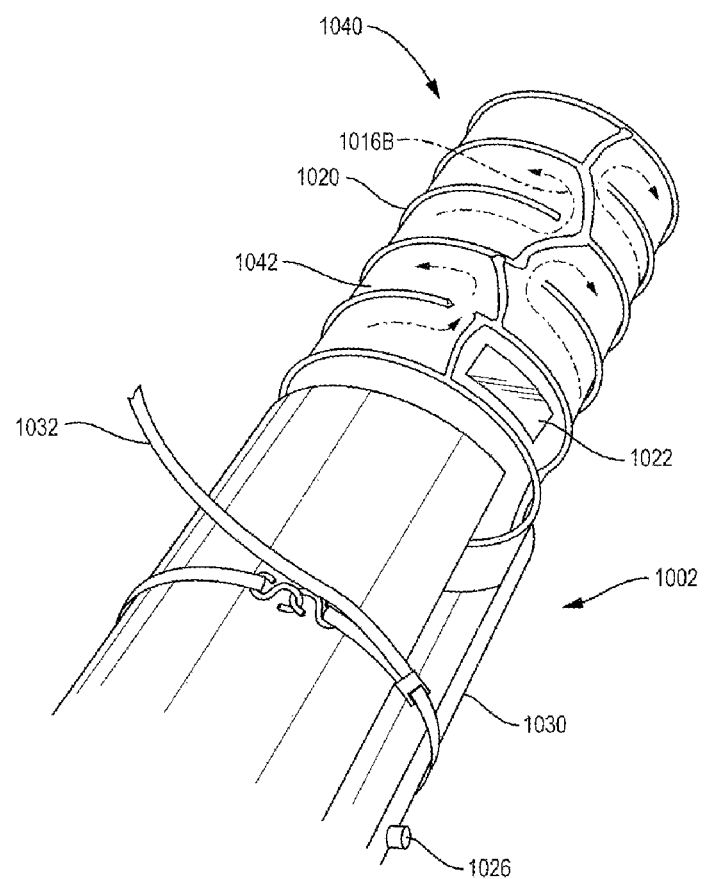
FIG. 3 is a perspective view of an exemplary embodiment of an exemplary heat exchange module having a jacketed, tiered baffle, bioreactor tank for routing a liquid coolant around the outer tank surface, the tank having a window.

FIG. 3 is a perspective view of an exemplary embodiment of a heat exchanger module 1002 somewhat similar to the structure shown in FIG. 2. A jacketed, tiered baffle, bioreactor tank 1002 includes an outer cylindrical-shaped jacket 1030; and a cylindrical tank 1040 having an inner tank surface defining a chamber configured for supporting a flexible bag (not shown) disposed within the chamber, and an outer tank surface having integral tiered baffles 1042 formed by protrusions 1020 and configured for routing a liquid coolant as shown by directional arrows 1016B around the entirety of the outer tank surface, the cylindrical tank 1040 disposed axially within the outer cylindrical-shaped jacket 1030, wherein the outer cylindrical-shaped jacket 1030 is sealed to the cylindrical tank 1040 in a manner sufficient to prevent or minimize loss of the liquid coolant that enters the system through port 1026. In constructing the system, strapping 1032 is used to help attach the jacket 1030 to the tank 1040 following its insertion in the jacket 1030.

The heat exchanger is formed from the inner, tiered, fluid channel 1042 and the outer support structure or outer vessel wall 1030, with the temperature control fluid flowing therebetween. The heat exchange module 1002 includes a vessel or inner vessel wall 1040 comprising an inner, tiered, fluid channel 1042. The inlet tube 1026 can be configured to allow temperature control fluid to enter the module 1002 formed by the barrel-shaped tank or vessel 1040 and the outer jacket 1030. Alternatively, the outer jacket 1030 can be conically formed, utilizing seals known in the art to seal the module 1002.

The embodiment including a jacketed, tiered baffle, bioreactor tank typically provides coolant to about 100 percent (100%) of the tank surface, conducting heat away from a flexible bag bioreactor disposed within the tank.

FIGS. 4A and 4B, as described in more detail above, illustrate that a temperature-controlling surface can comprise a thermally conductive surface formed of a thermally conductive material, such as, e.g., a plurality of particles 804, 814, FIGS. 4A, 4B, respectively.

Figure 5:
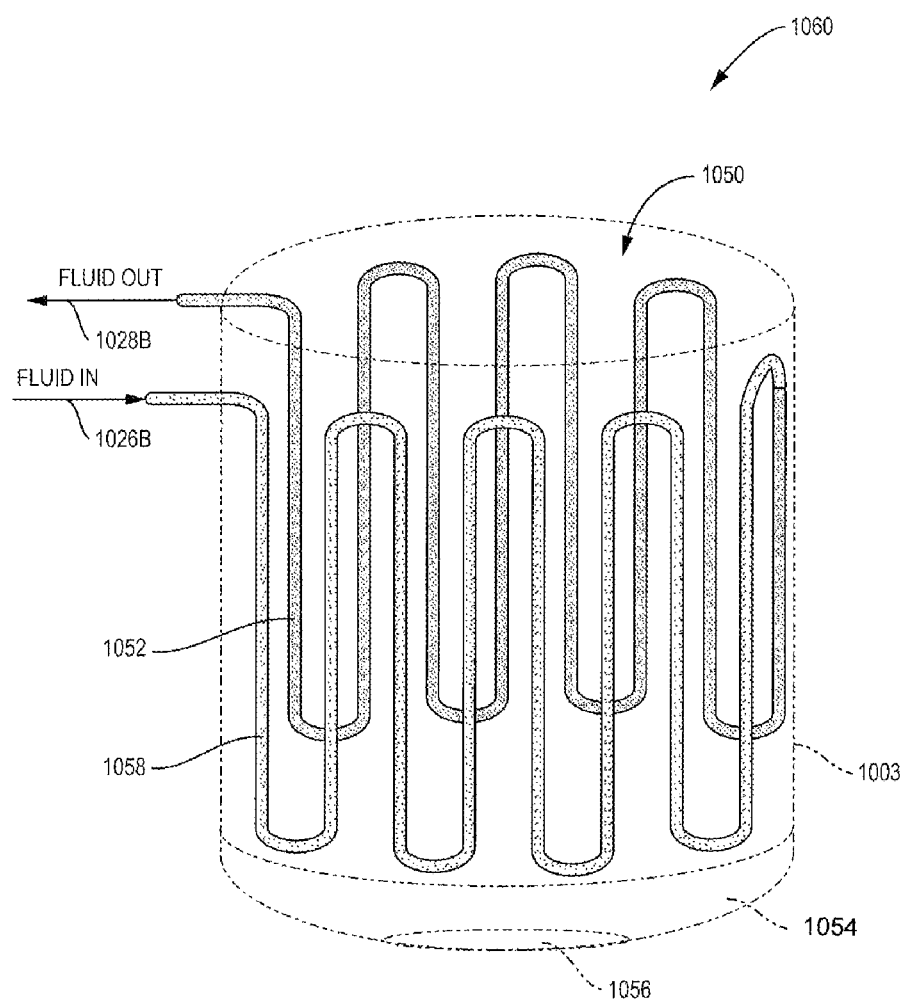
FIG. 5 is a schematic elevational view of an exemplary heat exchange module wherein metallic tubing for holding a heat exchange fluid is oriented in a serpentine manner around and against an inner wall of a reactor vessel or support structure.

FIG. 5 is a schematic elevational view of an exemplary heat exchange module 1060 wherein metallic tubing 1052, 1058 is oriented in a serpentine manner around and against a surface of inner wall 1050 of a reactor vessel 1003. In the embodiment shown, temperature control fluid enters tubing 1058 in a direction shown by arrow 1026B, exchanging heat with the container or bag (not shown) positioned within vessel 1003, and exiting from tubing 1052 which is fluidically connected to tubing 1058 of which is a portion of tubing 1058. The temperature control fluid is passed through the tubing in order to transfer heat to or from a flexible bag (not shown) which is positioned within the vessel 1003 and seated against the inner wall 1050 of the vessel.

The bottom 1054 of the vessel 1003 includes a portion 1056 which typically supports an external magnetic drive system that is magnetically coupled to an agitator within the flexible bag.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will readily appreciate that all parameters, dimensions, materials, and configurations described herein are meant to be exemplary and that the actual parameters, dimensions, materials, or configurations will depend upon the specific application for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention can be practiced otherwise than as specifically described and claimed. The present invention is directed to each individual feature, system, article, material, kit, and/or method described herein, and to any combination of the foregoing.

The indefinite articles "a" and "an," as used herein in the specification and in the claims, unless clearly indicated to the contrary, should be understood to mean "at least one." Throughout the description and claims of this specification, the words "comprise," "contain," "include," "having," "composed of," and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

It should also be understood that, unless clearly indicated to the contrary, in any methods claimed herein that include more than one step or act, the order of the steps or acts of the method is not necessarily limited to the order in which the steps or acts of the method are recited.

Features groups described in conjunction with a particular aspect of the invention are to be understood to be applicable to any other aspect described herein unless incompatible therewith. All of the features disclosed in the specification, and claims, abstract and drawings, and/or all of the steps of any method or process disclosed, can be combined in any combination, except combinations where at least some of such features or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. All publications and references cited herein are expressly incorporated herein by reference in their entirety.

What is claimed is:

1. A heat exchange module for use in a chemical, pharmaceutical or biological reactor system having a single use flexible container, the module comprising:
    a body having a central chamber configured for receiving the single use flexible container and configured to be disposed in a reactor vessel, the body comprising:
        an outer surface configured to conform to a shape of the reactor vessel;
        at least one thermally conductive surface adapted to contact the flexible container to facilitate heat transfer; and
        at least one integral baffle forming a protrusion into the central chamber such that when the flexible container is inserted into the chamber, a fluid within the flexible container is baffled by the at least one baffle,
        wherein the body is an elongate body having a top end and a bottom end and is adapted to be inserted into the reactor vessel such that the body extends at least a substantial portion of the distance between a top and a bottom of the reactor vessel; and
    a heat exchanger disposed at the outer surface of the body, the heat exchanger comprising a fluid circulation path through which a heat exchange fluid can be circulated around the circumference of the body and into and out of a channel in the at least one baffle, such that when the flexible container is inserted into the chamber, a fluid within the flexible container is heated or cooled by the heat exchange fluid and baffled by the at least one baffle.

2. The heat exchange module of claim 1, wherein the fluid circulation path comprises:
    an elongate tube or channel axially positioned at the outer surface of the body and extending substantially the length of the body, the elongate tube or channel configured for delivering the heat exchange fluid through the elongate tube or channel; and
    a flow path of the heat exchange fluid from the opening at the bottom of the elongate tube or channel to an outlet or an outlet tube at the top end of the body.

3. The heat exchange module of claim 1, wherein the body is configured to extend to a position opposite an impeller positioned at or near the bottom of the single use flexible container, and the at least one integral baffle configured to baffle a shear field produced by the impeller.

4. The heat exchange module of claim 1, wherein the heat exchange module is integrally formed as a part of the reactor vessel and wherein the at least one baffle comprises the thermally conductive surface adapted to contact the single use flexible container and to facilitate heat transfer.

5. The heat exchange module of claim 4, wherein the heat exchange module is integrally formed as part of the reactor vessel and the fluid circulation path further comprises at least one non-linear channel disposed within a wall of the reactor vessel.

6. The heat exchange module of claim 5, wherein the non-linear channel further comprises at least one of spiral, serpentine and maze-like pathways configured to maintain the thermally conductive surface at a desired temperature.

7. The heat exchange module of claim 1, wherein:
    the at least one baffle includes a separator plate positioned within the channel in the baffle;
    wherein the at least one separator plate is configured to prevent the heat exchange fluid from flowing vertically within the channel in the baffle.

8. The heat exchange module of claim 7, wherein:
    the at least one separator plate is a plurality of separator plates disposed within the channel in the baffle.

* * * * *